United States Patent [19]

Watanabe et al.

[11] 3,933,902

[45] Jan. 20, 1976

[54] METHOD FOR THE OPTICAL RESOLUTION OF DL-α-PHENYLGLYCINE

[75] Inventors: Teiko Watanabe, Tokyo; Shigeyoshi Hayashi, Kurhshiki; Shunji Ouchi, Tokyo; Saburo Senoo, Shiki, all of Japan

[73] Assignee: Asahi Kasei Kogyo Kabushiki Kaisha, Osaka, Japan

[22] Filed: Dec. 11, 1972

[21] Appl. No.: 313,729

[52] U.S. Cl....... 260/501.12; 260/518 R; 260/239.1
[51] Int. Cl.². ................................. C07C 143/26
[58] Field of Search........ 260/501.12, 518 R, 534 G

[56] References Cited
UNITED STATES PATENTS
3,646,082   2/1972   Ito et al. .................. 260/534 G
FOREIGN PATENTS OR APPLICATIONS
1,210,495   10/1970   United Kingdom
OTHER PUBLICATIONS
Santhaman, Chemical Abstracts, Vol. 74, (1971), Col. 42616.

Primary Examiner—James O. Thomas, Jr.
Assistant Examiner—G. Brethenstein
Attorney, Agent, or Firm—Sughrue, Rothwell, Mion, Zinn & Macpeak

[57] ABSTRACT

A method for obtaining an optically active α-phenylglycine benzenesulfonate by optical resolutions which comprises dissolving DL-α-phenylglycine benzenesulfonate in an aqueous solution of benzenesulfonic acid, cooling the resulting solution to a temperature sufficient to render the solution supersaturated, selectively crystallizing either optically active D- or L-α-phenylglycine benzenesulfonate in the presence of a seed of either D- or L-α-phenylglycine benzenesulfonate corresponding to the optically active α-phenylglycine benzenesulfonate to be crystallized out, and separating the resulting crystals from the liquid phase is disclosed.

14 Claims, 2 Drawing Figures

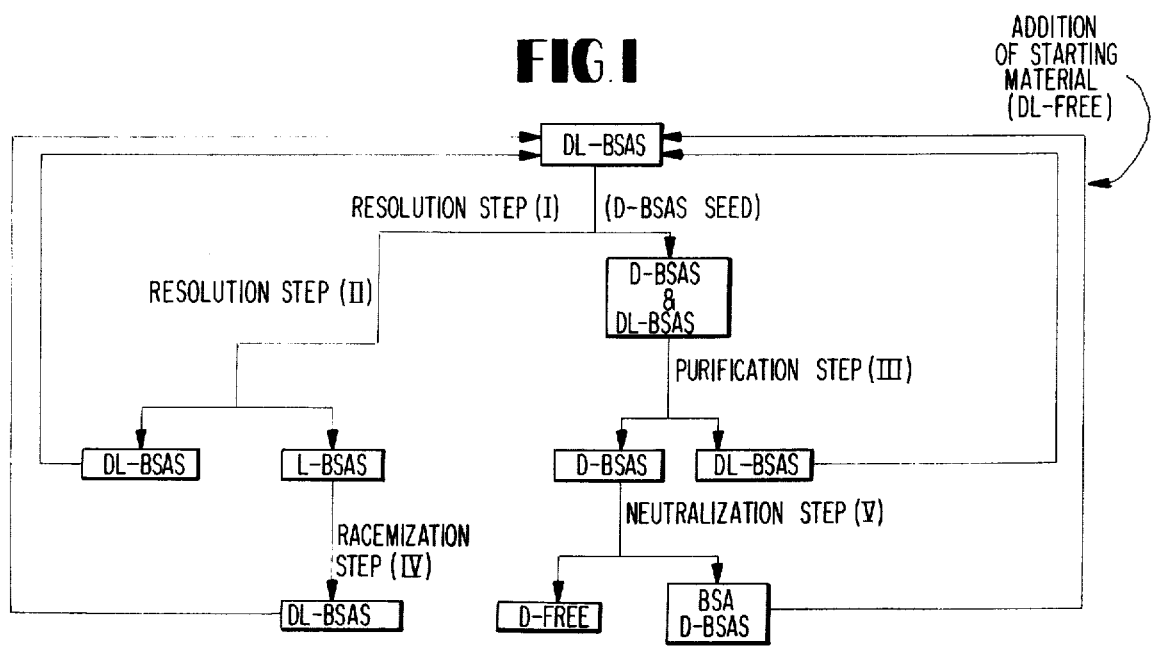
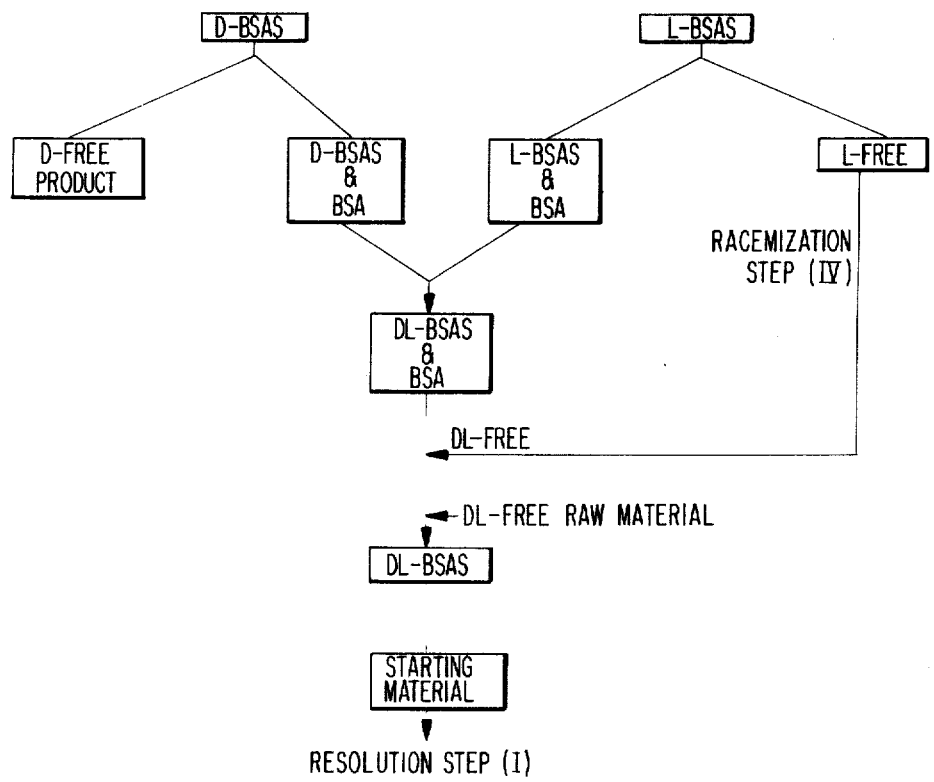

METHOD FOR THE OPTICAL RESOLUTION OF DL-α-PHENYLGLYCINE

BACKGROUND OF THE INVENTION

1. Field of the Invention

This invention relates to a method for the optical resolution of DL-α-phenylglycine. More particularly, this invention relates to a method for obtaining D-α-phelglycine by the optical resolution of DL-α-phenylglycine.

2. Description of the Prior Art

D-α-phenylglycine is known to be a useful starting material for preparing synthetic penicillins, in particular, ampicillin which has a broad antimicrobial spectrum, and a demand for a method for producing D-α-phenylglycine in large amounts and at low cost has increased in the field of synthetic penicillins as disclosed in J. Chem. Soc., 1962, pp 1440–1453 and U.S. Pat. No. 2,985,648.

The compound α-phenylglycine, one of the α-amino acids, is not a naturally occuring compound and is obtainable only by chemical synthesis. In conventional processes for the production of α-phenylglycine the product is usually a mixture of DL-forms comprising an equal proportion of the D-form and the L-form. It is well known that synthetic penicillin having an antimicrobial activity can be obtained only from the D-form and, therefore, the above DL-mixture should be optically separated to obtain only the D-form of α-phenylglycine.

Various procedures for the optical resolution of DL-α-phenylglycine have heretofore been proposed. Typical procedures include a method comprise reacting DL-α-phenylglycine with d-camphor sulfonic acid and fractionally crystallizing the two resulting diastereoisomers by taking advantage of the difference in their solubilities, a method comprising converting DL-α-phenylglycine into an N-formyl derivative thereof, reacting the thus obtained N-formyl derivative with brucine and separating the resulting diastereoisomers by taking advantage of the difference in their solubilities and a method comprising converting the DL-α-phenylglycine into an N-acyl derivative thereof, reacting the thus obtained N-formyl derivative with brucine and separating the resulting diastereoisomers by taking advantage of the difference in their solubilities and a method comprising converting the DL-α-phenylglycine into an N-acyl derivative thereof and separating the N-acyl derivative into the optically active components by the activity of microorganisms.

However, the above conventional procedures are disadvantageous in that they require complicated resolution operations and, when the resolution is conducted via diastereoisomers, they require specific reagents which must be optically active, and further recovery of the reagents using an acid or an alkali is necessary.

SUMMARY OF THE INVENTION

An object of this invention is to provide a method for easily producing D-α-phenylglycine on an industrial scale at low cost by the optical resolution of DL-α-phenylglycine.

Another object of this invention is to provide a method for continously obtaining D-α-phenylglyine from DL-α-phenylglycine without any substantial loss of raw materials.

These objects are accomplished by a process wherein DL-α-phenylglycine in the form of a benzensulfonate salt is subjected to resolution to give the D-α-phenylglycine salt and the L-α-phenylglycine salt, the D-salt is purified and neutralized to give D-α-phenylglycine (salt free) and the L-salt is subjected to racemization and reused as a raw material in the processing sequence.

The above objects and other objects of this invention will be understood with greater clarity from the descriptions given hereinafter.

BRIEF DESCRIPTION OF THE ACCOMPANYING DRAWINGS

FIG. 1 is a flow chart of the method of this invention wherein BSAS stands for α-phenylglycine benzenesulfonate, BSA stands for benzenesulfonic acid the abbreviations DL-, D- and L- indicate the racemic (DL-) and optically active forms (D- or L-) of α-phenyglycine and the term "free" indicates the DL-, D- or L- form is not in the salt form.

FIG. 2 is a flow chart showing detailed procedures for the conversion of D-BSAS into D-free, wherein BSAS, BSA and the term "free" are as defined previously.

DETAILED DESCRIPTION OF THE INVENTION

The inventors, as a result of research to accomplish the above objects discovered the following facts.

1. DL-α-phenylglycine forms a salt with benzenesulfonic acid. (For simplicity, the DL-α-phenylglycine benzenesulfonic acid salt is hereinafter referred to as DL-BSAS.) The infrared absorption spectrum and X-ray diffraction pattern of the crystalline DL-BSAS are fully consistent with those of an optically active α-phenylglycine benzenesulfonate crystal (hereinafter referred to as an optically active BSAS, or as D-BSAS or L-BSAS), indicating that the DL-BSAS is in the form of a crystalline racemic mixture.

2. α-phenylglycine differs from other α-amino acids in that it exhibits a weak ability to form salts due to the specific electronic structure of α-phenylglycine. In forming α-phenylglycine benzenesulfonate, α-phenylglycine can form a stable benzenesulfonate salt only when a stoichiometric excess of benzenesulfonic acid is present, that is, more than 1 mole of benzenesulfonic acid is present per mole of α-phenylglycine. More specifically, α-phenylglycine can form a stable salt with benzenesulfonic acid in a system having a concentration more than 5 g of benzenesulfonic acid per 100 g of water (at a pH less than 1.0). If the above condition is not satisfied, a partial dissociation of the salt which is formed will occur and free α-phenylglycine can be crystallized out. In accordance with the present invention, any pH lower than 1 can be utilized.

3. The solubility of DL-BSAS in an aqueous benzenesulfonic acid having a concentration within the above range is greater than that of an optically active BSAS, the ratio of solubility being approximately 2 times.

4. The optically active BSAS is not dissolved in a saturated aqueous solution of DL-BSAS. The heterogeneous equilibrium of the aqueous solution consisting of DL-BSAS, L-BSAS and BSA (benzenesulfonic acid) are shown in Table 1 below.

Table 1

Heterogeneous Equilibrium of Aqueous Solution consisting of DL-BSAS, L-BSAS and BSA (determined at 10°C and 30°C)

| Concentration of BSA g/100g water | Type of solid precipitated crystals | Solubility g/100g solvent* 10°C | Solubility g/100g solvent* 30°C | Optical Rotation Determined |
|---|---|---|---|---|
| 20 | L-BSAS | 4.55 | 10.8 | — |
| 20 | DL-BSAS | 7.44 | 18.7 | — |
| 20 (Racemic) | DL-BSAS L-BSAS | 7.41 | 18.7 | 0 |
| 10 | L-BASA | 5.95 | 14.1 | — |
| 10 | DL-BSAS | 10.20 | 24.2 | — |
| 10 (Racemic) | DL-BSAS+L-BSAS | 10.21 | 24.2 | ≈0 |

*When 20 g of BSA is used, the solvent consists of 83.4 weight percent of water (100 g water/120 g total weight) and 16.6 weight percent of BSA (20 g BSA/120 g total weight) and, when 10 g BSA is used, the solvent consists of 90.9 weight percent of water (100 g water/110 g total weight) and 9.1 weight percent of BSA (10 g BSA/110 g total weight).

The invariable point of the above heterogeneous system is consistent with the equilibrium value of an aqueous solution consisting of DL-BSAS and BSA. This indicates that the crystals of DL-BSAS are a racemic mixture of L-BSAS crystals and D-BSAS crystals.

5. When a liquid phase containing a mixture of DL-BSAS and an optically active BSAS (for example, L-BSAS) in a solvent, which does not react with the above salts (DL-BSAS and L-BSAS) and which does not dissociate the salts i.e., an aqueous solution of BSA having a concentration more than 5 g of BSA per 100 g of water, which may contain a small amount (less than 50% by volume) of a lower alkanol having 1 to 3 carbon atoms, acetone or dioxane, or a mixture thereof, is brought into a state of saturation (the terms saturation and equilibrium will be used interchangeably) with respect to DL-BSAS, L-BSAS separates as a solid phase from DL-BSAS as a liquid phase. Thus, the above two compounds can be separated quantitatively from each other by solid-liquid separation to obtain each of the compounds having a high optical purity. Although L-BSAS was exemplified above, the same effect is encounted with D-BSAS.

6. When a solution having dissolved therein DL-BSAS and an optically active BSAS (for example, L-BSAS) is combined with crystals of DL-BSAS in an amount of at least two times the amount of L-BSAS by weight and the resulting solution is maintained in a state of saturation with respect to the total DL-BSAS, only D-BSAS (an antipode to L-BSAS which has been dissolved in the solution) of the added DL-BSAS is selectively dissolved in the solution and L-BSAS which has the same optical activity as that of the optically active component which has been dissolved in the solution is not dissolved in the solution and remains as crystals.

7. When one of the optically active BSAS forms, for example, L-BSAS, is heated at a temperature in the range of from 110° to 200°C under pressurized conditions, i.e., 1 to 30 atmospheres, in an aqueous solution of benzenesulfonic acid having a concentration greater than 5 g of BSA per 100 g of water, the L-BSAS is converted into a racemic mixture of DL-BSAS. Also, free α-phenylglycine can be converted into the DL-form in the presence of water by merely heating α-phenylglycine at a temperature in the range of from 180° to 220°C under pressurized condition, i.e., 1 to 30 atmospheres.

8. When the conditions recited in (2) above are not satisfied, α-phenylglycine benzenesulfonate in either the D- or L-form dissociates into the free D- or L-form of α-phenylglycine and benzenesulfonic acid. The degree of dissociation generally increases as the amount of water present increase, but the amount of water can appropriately be adjusted, i.e., use a small amount of water sufficient to avoid excess dissolution of free α-phenylglycine which is slightly soluble in water, to obtain free α-phenylglycine. For example, the amount of free D-α-phenylglycine obtained from 10 g of D-α-phenyglycine benzenesulfonate by adding 50, 100, 200 and 500 ml of water at a temperature of 15°C is 1.8, 2.4, 2.9 and 2.6 g, resepctively.

When the dissociation of BSAS is incomplete, the solution from the dissociation step may be rendered neutral with an alkali such as an aqueous sodium hydroxide solution or aqueous ammonia, etc. The alkali is generally used in an amount equal to the amount of BSAS present.

The present invention is based on the discoveries summarized in (1) to (8) above, and the purposes of the present invention can be accomplished by a combination of the above discoveries. That is, as shown in the flow charts described hereinafter, this invention provides not only a method for resolving DL-α-phenylglycine into the D-form and the L-form (Resolution Steps I and II), but also a method for obtaining the desired D-form in a highly purified state (Purification Step III) as well as a method for the racemization of the undersirable L-form for reuse as a starting material in the separation step of this invention and a method for converting D-α-phenylglycine benzenesulfonate into free D-α-phenylglycine.

The above steps of the present invention are described hereinafter in greater detail.

RESOLUTION STEP (I)

Recovery of D-BSAS

The resolution may be conducted by either first crystallizing the D-form and then crystallizing the L-form or first crystallizing the L-form and then crystallizing the D-form. Substantially the same procedure can be used in these alternative separations. The procedure for the separation will be described hereinafter by referring to the procedure where the D-form is first crystallized, keeping in mind that the procedure can be equally applied to the case where the L-form is first crystallized merely by altering the initial seed composition to that of the L-form.

Briefly, the resolution comprises first converting DL-α-phenylglycine into the benzenesulfonic acid salt thereof by mixing DL-α-phenylglycine with benzenesulfonic acid under the conditions heretofore described at point (2), dissolving DL-α-phenylglycine benzenesulfonate in an aqueous solution of benzenesulfonic acid to the extent of supersaturation and selectively crystallizing D-BSAS using a seed crystal of D-BSAS. Again, the aqueous solution of benzenesulfonic acid may contain less than 50% by volume of a lower alkanol having 1 to 3 carbon atoms, acetone, dioxane, or a mixture thereof. When the super-saturated DL-BSAS solution is seeded with crystals of D-BSAS, crystallization of only D-BSAS selectively occurs and crystals of D-BSAS are formed over a period of time. Then, after that period of time, crystallization of the L-form begins and crystals of the L-form precipitate. Ultimately, crystallization of both the D- and L-forms simultaneously occurs until the crystallization system reaches its equilibrium at the resolution temperature. To attain an efficient resolution of the D-form, it is necessary to conduct a solid-liquid separation during the crystallization of only D-BSAS, i.e., prior to the commencement of the crystallization of L-BSAS. The phase during which crystals having the same optical activity as that of the seed cyrstals are predominantly crystallized is referred to as the "resolution time". The resolution time is determined mainly depending upon the degree of supersaturation and the amount of seed crystals used. The higher the degree of supersaturation, the higher the rate of separation. Also, the larger the amount of seed crystals, the higher the rate of resolution. When the degree of supersaturation is excessively high, crystallization sometimes occurs not only in the seeded optical form but also in the non-seeded optical form of α-phenylglycine. For this reason, in the method of this invention, a suitable degree of supersaturation as defined hereinafter is from 105% to 200%, preferably about 105 to 150%.

$$\text{Supersaturation} = \frac{\text{Amount of DL-BSAS dissolved (g) per 100 g of solvent*}}{\text{Amount of DL-BSAS dissolved (g) per 100 g of solvent* at saturation}} \times 100$$

*An aqueous solution of benzenesulfonic acid (5 gl/100 g water) which may contain less than 50% by volume of a lower alkanol having 1 to 3 carbon atoms, acetone, dioxane or a mixture thereof.

As previously described, the higher the amount of seed crystals, the higher the rate of resolution. The proportion of the seed crystals can be from 100% to 5% by weight based on the weight of DL-BSAS dissolved in the solution to be separated, but generally the proportion is less than 20%, preferably from 5% to 20% by weight based on the weight of DL-BSAS dissolved.

It is also possible to add additional seed crystals after the initiation of the crystallization of the D- or L- form, and this may be done either in seed crystal-initiated crystallization or in those crystallization where seed crystals are not used.

The resolution can be carried out at a temperature in the range of from 0° to 100°C when water is used as a solvent, but in order to minimize the loss of water in the filtration of the crystals and to avoid economic disadvantages, such as additional heating means, it is advantageous to carry out the resolution near room temperature.

Stirring can advantageously be used during the resolution so as to uniformly disperse the seed crystals which are used as an aid for the crystallization in the liquid phase. However, vigorous agitation or friction which would lead to the crystallization of L-BSAS (in the case where the crystallization of D-BSAS only is desired) should be avoided.

The supersaturation may be accomplished by any conventional procedure such as by cooling or by evaporation of the solvent, but cooling is generally preferred since the composition of the solvent can be maintained constant.

Seed crystals can be used in either the dried state or in the wet state, i.e., moistened with the same solvent as that used in the separation. In particular, wet seeds are advantageous in that they tend to uniformly disperse in the separation solution.

In some cases, the seeds may be added as a solution sufficiently concentrated to upset the saturation of the system to be crystallized or may be previously dissolved in a solution of the DL-BSAS to be separated prior to the saturation thereof. This means that the mother liquor from which the D-BSAS has been separated may be reused in another batch of starting resolution solution with or without adding additional DL-BSAS crystals to the recycled solution so long as the solution is supersaturated with respect to DL-BSAS.

Any aqueous solution of benzenesulfonic acid having a concentration greater than 5 g per 100 g can be used in principle as a separation solvent. However, at higher concentrations, the increased viscocity of the solution tends to prevent the formation of the desired crystals, and further the amount of DL-BSAS dissolved is decreased whereby an effective separation cannot be obtained. For this reason, a concentration of benzenesulfonic acid from 5 to 30 g per 100 g of water is advantageous with the preferred range being from 10 g to 20 g per 100 g of water.

When the supersaturation, the type of seed crystals and the separation temperature are selected appropriately in the manner described above, the separation is generally completed within the range of from 1 to 60 minutes. Under the above conditions, D-BSAS can be selectively crystallized from the resolution solution of DL-BSAS, and the solid phase separated from the liquid phase.

The above resolution step can be carried out in a batch manner or a continuous manner.

RESOLUTION STEP (II)

Recovery of D-BSAS

The mother liquor from which D-BSAS has been separated as described above is rich L-BSAS and L-BSAS can be recovered therefrom by taking advantage of the discovery previously described at (5). In greater detail, the mother liquor is first maintained at a temperature at which DL-BSAS is saturated followed by stirring gently to crystallize L-BSAS. After substantially all L-BSAS has been crystallized as evidenced by the 0 value of optical rotation of the mother liquor, the crystals of L-BSAS precipitated are recovered by an appropriate procedure, e.g., filtration.

The DL-BSAS solution obtained after separation of L-BSAS can be used as a starting solution in the resolution step (I) after additional DL-BSAS crystals have been added to the solution, i.e., in an amount equal to the total amount of D-BSAS plus L-BSAS previously recovered in Resolution Step (I) and Resolution Step (II).

Alternatively, when DL-BSAS is dissolved in an aqueous solution of benzenesulfonic acid at a benzenesulfonic acid concentration greater than 5 g per 100 g of water having dissolved therein L-BSAS (the L-rich mother liquor from Resolution Step (I)) without causing the precipitation of L-BSAS and the mixture is brought into supersaturation with respect to DL-BSAS, the dissolved L-BSAS can be crystallized predominantly over DL-BSAS whereby the resolution is commenced. The crystallization of only L-BSAS is followed by separation of the crystals. This results in producing a mother liquor which is rich in D-form and the mother liquor can be worked up to obtain D-BSAS in a manner similar to that used to obtain L-BSAS merely by adding DL-BSAS crystals as a starting material equal to the amount of the D- and L-forms removed in Resolution Step (I) and Resolution Step (II), whereby the separation can be continued without using seed crystals. For instance, DL-BSAS crystals are added to the L-rich mother liquor from Resolution Step (I), from which D-BSAS has been removed, in an amount equal to the total amount of D-BSAS removed and L-BSAS present in the mother liquor whereafter the resolution is commenced. These separations can be operated alternately to separate L-BSAS and D-BSAS crystals from the racemic DL-BSAS starting material without using seed crystals of L-BSAS or D-BSAS.

Further, the result previously described in (6) can be used in this separation step. In this case, the separation can be attained by merely adding DL-BSAS as a raw material without using seed crystals. This method is more advantageous from the standpoint of the heat source than the case where all the added DL-BSAS is dissolved since much heat will be required for dissolving all the added DL-BSAS as compared with the case where only either one of the optically active salts is dissolved. This method is also advantageous in that the method utilizes the tendency of only one of the optically active components of DL-BSAS to dissolve and, therefore, this method makes it possible to control the grain size of the crystals produced by adjusting the grain size of the DL-BSAS crystals used as a starting material.

PURIFICATION STEP (III)

When the crystals of D-BSAS obtained in resolution step (I) contain an unacceptable amount of DL-BSAS, an appropriate solvent, i.e., an aqueous solution of BSA, in an amount sufficient to dissolve the DL-BSAS contaminant is added to the impure D-BSAS and the mixture is brought to the equilibrium state with respect to DL-BSAS according to the principle previously described in (5) whereby D-BSAS is separated as crystals from the contaminant DL-BSAS which remains in the liquid phase. This purification can be carried out at the same temperatures as is used in the separation step, i.e., at a temperature in the range of from 0° to 100°C, but is advantageously carried out at approximately room temperature. The solvent used in the purification is an aqueous benzenesulfonic acid solution (the mixed solvent systems heretofore described may also be used) having a concentration as recited in (2). If the above equilibrium cannot be attained in view of the fact that the DL-BSAS contaminant is present in a small amount and the solvent is used in a small amount which is not sufficient to stir the mixture efficiently, an appropriate amount of a saturated solution of DL-BSAS may be added to the mixture to be purified at a temperature where the purification is conducted, i.e., an amount which permits the system to be adequately mixed or stirred in order to bring the system to equilibrium between the solid and liquid phases.

A purification utilizing the same principles may be performed on crystals of L-BSAS when necessary or desired, but since L-BSAS is generally racemized in the present process, such a purification will seldom, if ever, be used.

RACEMIZATION STEP (IV)

Among the optically active components obtained from resolution steps (I) and (II), L-BSAS can be used as a starting material after it is racemized. The racemization of L-BSAS can be carried out, without dissociating benzenesulfonic acid, by heating L-BSAS at a temperature in the range of from 110° to 200°C, preferably 180°C, in a solvent, i.e., an aqueous solution of BSA having a concentration more than 5 g of BSA per 100 g of water, for a period of from 2 to 10 hours thereby yielding a racemic DL-BSAS. The L-BSAS to be racemized and the solvent can be used in any proportions, but a ratio of from about 0.5 to about 6 parts by weight of solvent per 1 part by weight of L-BSAS can advantageously be used since the above recited ratio makes it possible to obtain racemic DL-BSAS as a crystalline solid by merely cooling the racemization mixture and to reuse the reaction mother liquor repeatedly.

There is a close correlation between the racemization temperature and the racemization time, but generally the racemization is completed under pressurized conditions, i.e., 1 to 30 atmospheres at a temperature of 160°C for about 6 hours or at a temperature of 180°C for about 2 hours.

The desired racemization product, DL-BSAS, can be isolated as crystals by cooling the racemization mixture, crystallizing DL-BSAS and conducting a solid-liquid separation, and the resulting mother liquor can then be recycled to the separation step after additional starting DL-BSAS is added thereto.

As shown in FIG. 2, free L-α-phenylglycine obtained from resolution Step II can also be subjected to the racemization step to obtain a racemic DL-free form. This racemization can be carried out in a manner similar to that described for the racemization of L-BSAS. However, for the racemization of free L-α-phenylglycine, it is advantageous to use a temperature in a range of from 150° to 220°C under a pressure of from 1 to 30 atmospheres for a period of from 2 to 10 hours and a ratio of from 0.5 to about 10 parts by weight of the solvent per 1 part by weight of free L-α-phenylglycine.

RECOVERY OF FREE D-α-PHENYLGLYCINE FROM D-BSAS (V)

According to the principle previously described in (8), free D-α-phenylglycine in crystalline form can be obtained by merely dissolving D-BSAS in water, thereby dissociating the anion portion of the salt. However, there is a problem in this step in that the dissociation of the anion portion of the salt cannot be accomplished completely, i.e., while the neutralization may be effected without using acids or alkalis, the resulting neutralized solution may contain BSA and L- (or D-) BSAS. When this solution is recycled to the Resolution Step, the resolution system would be rich in L- (or D-) BSAS. To avoid this unbalance, the procedure illustrated in FIG. 2 is applied so that all the BSA can be recycled to the resolution system without causing an unbalance in the amount of D- and L-BSAS. The procedure illustrated in FIG. 2 will now be explained in greater detail.

The optically active BSAS materials obtained from resolution step (I), followed by Purification Step (III), if necessary, and resolution step (II), i.e., D-BSAS and L-BSAS, are separately dissolved in an equal amount of water to obtain crystals of the free α-phenylglycine form in each solution. In this case, D-BSAS and L-BSAS are used in an equal amount and dissolve in an equal amount. After separation of the resulting crystals from each of the solutions, the solutions containing BSA and either D-BSAS or L-BSAS which remained undissociated are combined to form a solution containing DL-BSAS and BSA. The resulting solution can then be recycled to resolution step (I). In this manner, the amount of BSA in the separation system can be maintained constant.

The present invention is further illustrated by the following examples but they are not to be construed as limiting the scope of this invention.

EXAMPLE 1

Resolution Step (I)

43.6 g of DL-BSAS was dissolved in 205 g of an aqueous solution of benzenesulfonic acid having a concentration of 10 g of benzenesulfonic acid per 100 g of water, and the resulting solution was cooled to a temperature of 18°C. 0.8 g of wet crystals of D-BSAS were then added to the solution and the mixture was allowed to crystallize at that temperature for a period of 8 minutes by allowing the solution to stand following by filtration. The resulting crystals of D-BSAS were then washed with a small amount of an aqueous solution of benzenesulfonic acid having the same benzenesulfonic acid concentration as above which had been cooled to 5°C to yield 3.58 g of crystals. The resulting crystals had a specific rotatory power of −78.2° (c=1.0 in an aqueous benzenesulfonic acid, 20 g/100 g water) and were found to be approximately 100% D-BSAS.

Neutralization Step 3.5 g of the above obtained crystalline D-BSAS was suspended in 20 ml of water and 1N aqueous ammonia was added to the suspension in an amount sufficient to adjust the pH to 6.8. The mixture was stirred for 3 hours at a temperature of 15°C, and filtered to separate the precipitated crystals. The crystals were then washed with a small amount of cold water and then dried to yield 1.7 g of crystals. The crystals showed a specific rotatory power of $[\alpha]_D^{20} = -158°$ (c=1 in 6N.HCl) and were found to be pure D-α-phenylglycine (D-free crystals).

Resolution Step (II)

To 234 g of the mother liquor from the resolution step (I), which contained 38 g of DL-BSAS and 2.8 g of L-BSAS in an aqueous benzenesulfonic acid having a concentration of 10 g of benzenesulfonic acid per 100 g of water, there was added 5.6 g of crystals of DL-BSAS while maintaining the temperature at 30°C. The mixture was then stirred for 30 minutes at that temperature to bring the mixture to equilibrium, and a solid-liquid separation performed by filtration under reduced pressure using a suction flash to obtain 2.86 g of crystals. The resulting crystals had a specific rotatory power of +78.1° (c=0.51 in an aqueous benzenesulfonic acid solution, 20 g/100 g water) and were found to be L-BSAS. The liquid obtained from the above solid-liquid separation had a specific rotatory power of 0° and it was confirmed that the liquid contained a racemic salt.

This liquor may be used as a starting solution in resolution step (I) by adding additional starting material, DL-BSAS crystals, which is to be subjected to optical resolution.

Racemization Step (IV)

2.5 g of the L-α-phenylglycine benzenesulfonate obtained in the resolution step (II) above were suspended in 50 ml of an aqueous solution of benzenesulfonic acid having a concentration of 20 g of benzenesulfonic acid per 100 g of water, and the suspension was heated at 160°C for 8 hours in a closed autoclave under autogenous pressure. After being cooled, the reaction mixture was found to have a specific rotatory power of approximately 0 indicating that the α-phenylglycine in the reaction mixture was completely converted into the racemic form.

EXAMPLE 2

Resolution Step (I) and Resolution Step (II)

250 g of DL-BSAS was dissolved in 1 Kg of an aqueous solution of benzenesulfonic acid having a concentration of 10 g per 100 g of water at a temperature 35°C, and the resulting solution was cooled to a temperature of 25.5°C. 4.5 g of wet crystals of L-BSAS was then added to the solution and the mixture was stirred gently at 25.5°C for 13 minutes. The precipitated crystals of L-BSAS which formed were filtered and the filtrate was then stirred gently for an additional 5 hours at 25.5°C to allow the precipitation of crystals of D-BSAS. The yield of the two crystals was 29.8 g (L-BSAS) and 24.4 g (D-BSAS), respectively, and the specific rotatory power of the crystals was found to be +78.1° and −78.0°, respectively (c=0.5 in an aqueous benzenesulfonic acid solution, 20 g/100 g water).

Neutralization Step (V)

Preparation of free D-α-phenylglycine from D-BSAS 400 ml of water was added to 28.0 g of crystals of D-BSAS obtained from the above resolution step (II), and the mixture was stirred for 1.5 hours at a temperature of 15°C. The precipitated crystals were then filtered to obtain 10.5 g of crystalline D-α-phenylglycine having a specific rotatory power of −158.1° (at 20°C, c=0.5 in 6N.HCl).

Racemization Step (IV)

100 ml of a saturated aqueous solution of DL-BSAS at a temperature of 15°C was added to 23.0 g of L-BSAS obtained from the above resolution step (II), and the mixture was heated at a temperature of 180°C for 3 hours in an autoclave under autogenous pressure to complete the racemization. After completion of the racemization, the resulting reaction product was transferred to a beaker and allowed to stand overnight, and the crystals formed were then filtered to obtain 28.8 g of crystals. The thus obtained crystals had a specific rotatory power of 0, indicating that the product is completely in the racemic form.

EXAMPLE 3

Resolution Step (I)

30 g of crystals of DL-BSAS were dissolved in 300 g of an aqueous solution of benzenesulfonic acid having a concentration of 30 g of benzenesulfonic acid per 100 g of water and the solution was cooled to 15°C. To the resulting supersaturated aqueous solution was then added 0.5 g of crystals of D-BSAS, and the crystals were allowed to grow while stirring at that temperature. After crystallization for 3 minutes, the precipitated crystals were filtered to obtain 5.0 g of D-BSAS crystals having a specific rotatory power of −54.6° (c=1 in an aqueous benezenesulfonic acid solution, 20 g/100 g water) and a 70% optical purity.

Purification Step (III)

To 5.0 g of the above obtained crystals there was added 100 ml of an aqueous solution of benzenesulfonic acid having a concentration of 10 g of benzenesulfonic acid per 100 g of water, and the mixture was stirred for 1 hour at a temperature of 18°C to bring the solution to equilibrium. The solution was filtered to obtain 3.3 g of D-BSAS having an optical rotatory power of −71° (c=0.97 in an aqueous benzenesulfonic acid solution, 20 g/100 g water).

Neutralization Step (V)

To 3.0 g of the crystals obtained above there was added 50 ml of water (undissolved crystals were partially present in the resulting solution), and the mixture was adjusted to a pH of 6.8 with 1N aqueous ammonia. After standing for 30 minutes, the precipitated crystals were filtered to obtain 1.2 g of crystalline D-α-phenylglycine having a specific rotatory power of +147° (c=1 in 6N hydrochloric acid).

Resolution Step (II)

To the mother liquor obtained from the resolution step (I) above was added 8.0 g of DL-BSAS followed by heating to dissolve the DL-BSAS. The resulting solution was slowly cooled to 15°C over a 10 minute period. During the cooling a number of crystal nuclei were produced and grown, and immediately thereafter the crystals formed were filtered to obtain 8.6 g of crystalline L-BSAS having a specific rotatory power of +77.8° (c=0.87 in an aqueous benzenesulfonic acid solution, 20 g/100 g water).

Racemization Step (IV)

8.0 g of L-BSAS crystals obtained above was added to 100 ml of a saturated solution of DL-BSAS in an aqueous benzenesulfonic acid having a concentration of 20 g benzenesulfonic acid per 100 g of water, and the mixture was heated in an autoclave under autogeous pressure at a temperature of 170°C for 5 hours followed by standing overnight at 15°C. There was obtained 7.8 g of crystals of DL-BSAS having an optical rotation of $[\alpha]_D^{20} = 0$ (c=0.5 in an aqueous benzenesulfonic acid solution, 20 g/100 g water).

EXAMPLE 4

5 g of crystals of L-BSAS was dissolved in 100 ml of an aqueous solution of benzenesulfonic acid having a concentration of 10 g per 100 g of water. The solution was then separated into three portions, and these solutions were heated at temperatures of 120°C, 140°C and 160°C, respectively, under autogenous pressure in an autoclave for a period of 5 hours. After cooling, the optical rotation of the resulting solutions was determined and the percent racemization was found to be 22⅔%, 50% and 95%, respectively.

EXAMPLE 5

32 g of crystals of L-BSAS were added to 100 ml of an aqueous solution of benzenesulfonic acid having a concentration of 20 g of benzenesulfonic acid per 100 g of water. The mixture was then heated in an autoclave at a temperature of 160°C for 6 hours under autogenous pressure. After cooling, the solution was allowed to stand overnight at room temperature and the precipitated crystals were filtered to obtain 15.8 g of crystals. The optical rotation was found to be 0, indicating complete racemization.

EXAMPLE 6

To the mother liquor obtained in Example 5 were added 32 g of crystals of L-BSAS, and the mixture was heated in an autoclave at a temperature of 180°C for 3 hours followed by racemization in the same manner as described in Example 5. There was obtained 31.8 g of crystals having an optical rotation of 0, indicating complete racemization.

EXAMPLE 7

To 5.0 g of L-α-phenylglycine there were added 200 ml of water, and the resulting solution was divided into four portions. These solutions were then heated in an autoclave at temperatures of 110°C, 150°C, 180°C and 220°C, respectively. After allowing the solutions to cool to room temperature, water was removed under reduced pressure to dryness and the optical rotation of the thus obtained residues was determined. The results indicated that the percent racemization in each of the residue was 0%, 21%, 36% and 88%, respectively.

While the invention has been described in detail and with reference to specific embodiments thereof, it will be apparent to one skilled in the art that various changes and modifications can be made therein without departing from the spirit and scope thereof.

What is claimed is:

1. A method for obtaining an optically active α-phenylglycine benzenesulfonate by optical resolution which comprises dissolving DL-α-phenylglycine benzenesulfonate in an aqueous solution of benzenesulfonic acid having a concentration greater than 5g of benzenesulfonic acid per 100 g of water, rendering the solution supersaturated, selectively crystallizing either optically active D- or L-α-phenylglycine benzenesulfonate, crystallization at least being initiated in the presence of a seed of either D- or L-α-phenylglycine benzensulfonate corresponding optically to the optically active α-phenylglycine benzenesulfonate to be crystallized out, and separating the resulting crystals from the liquid phase before initiation of crystallization of the optically active α-phenylglycine benzenesulfonate having an optical activity opposite to that of the crystallized optically active α-phenylglycine benzenesulfonate.

2. A method according to claim 1, wherein said aqueous solution of benzenesulfonic acid has a concentration in the range of 5 g to 30 g benzenesulfonic acid per 100 g of water.

3. A method according to claim 1, wherein said supersaturation is greater than 105% saturation.

4. A process according to claim 1, wherein said supersaturation is in the range of from 105% to 150% saturation.

5. A method according to claim 1, wherein said seed is prepared by adding crystals of DL-α-phenylglycine to an aqueous solution of an optically active α-phenylglycine benzenesulfonate, saturating the resulting solution with respect to total DL-α-phenylglycine benzenesulfonate, thereby crystallizing α-phenylglycine benzenesulfonate having the same optical activity as that of the α-phenylglycine benzenesulfonate initially present in the solution and separating the resulting crystals, said crystals of DL-β-phenylglycine being added in an amount of at least 2 times the amount of the optically active α-phenylglycine initially present in the solution.

6. A method according to claim 1, wherein said seed is used in an amount of from 5 to 100% by weight based on the weight of the dissolved DL-α-phenylglycine benzenesulfonate.

7. A method according to claim 1, wherein said crystallized product comprises optically active α-phenylglycine benzenesulfonate contaminated with DL-α-phenylglycine benzenesulfonate, and said method comprises the additional step of dissolving the contaminated optically active α-phenylglycine benzenesulfonate in an aqueous solution of benzenesulfonic acid having a concentration greater than 5 g per 100 g of water, substantially saturating the solution with respect to DL-α-phenylglycine benzenesulfonate contained therein, thereby crystallizing out said optically active α-phenylglycine benzenesulfonate, and separating the resulting optically purified crystals of α-phenylglycine benzenesulfonate.

8. A method according to claim 1, wherein said method further comprises saturating said liquid phase containing an optically active α-phenylglycine benzenesulfonate and DL-α-phenylglycine benzenesulfonate with respect to DL-α-phenylglycine benzenesulfonate without adding additional DL-α-phenylglycine benzenesulfonate thereby crystallizing out said optically active α-phenylglycine benzenesulfonate.

9. A method according to claim 1, wherein said saturation is carried out by cooling the liquid phase.

10. A method according to claim 1, which further comprises heating the resulting optically active α-phenylglycine benzenesulfonate having an undesired optical activity in an aqueous solution of benzenesulfonic acid having a concentration greater than 5 g per 100 g of water at a temperature in the range of from 110° to 200°C under pressurized condition in a sealed vessel to obtain a racemic DL-α-phenylglycine benzenesulfonate.

11. A method for the racemization of L-α-phenylglycine which comprises heating L-α-phenylglycine at a temperature in the range of from 180° to 220°C in the presence of water in an amount of from 0.5 to 50 parts by weight per 1 part by weight of said L-α-phenylglycine.

12. A method according to claim 1, wherein said method further comprises adding the resulting crystals of optically active α-phenylglycine benzenesulfonate to water in an amount of from 0.5 to 50 parts by weight per 1 part by weight of said α-phenylglycine benzenesulfonate to obtain an optically active free α-phenylglycine and benzenesulfonic acid.

13. A method according to claim 1, wherein said seed is used in an amount of from 5 to 20% by weight based on the weight of the dissolved DL-α-phenylglycine benzenesulfonate.

14. A method according to claim 1, wherein said method further comprises saturating said liquid phase containing an optically active α-phenylglycine benzenesulfonate and DL-α-phenylglycine benzenesulfonate with respect to DL-α-phenylglycine benzenesulfonate by adding additional DL-α-phenylglycine benzenesulfonate thereby crystallizing out said optically active α-phenylglycine benzenesulfonate.

* * * * *